US006716602B2

(12) United States Patent
Andersen et al.

(10) Patent No.: US 6,716,602 B2
(45) Date of Patent: Apr. 6, 2004

(54) METABOLIC RATE SHIFTS IN FERMENTATIONS EXPRESSING RECOMBINANT PROTEINS

(75) Inventors: Dana Andersen, Redwood City, CA (US); John Joly, San Mateo, CA (US); Bradley R. Snedecor, Portola Valley, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 10/000,655

(22) Filed: Nov. 1, 2001

(65) Prior Publication Data
US 2002/0164700 A1 Nov. 7, 2002

Related U.S. Application Data
(60) Provisional application No. 60/245,962, filed on Nov. 3, 2000.

(51) Int. Cl.⁷ .............................................. C12P 21/06
(52) U.S. Cl. .................... 435/69.1; 435/69.4; 435/71.2; 435/252.8; 435/243
(58) Field of Search ............................. 435/69.1, 69.4, 435/71.2, 252.8, 243

(56) References Cited

U.S. PATENT DOCUMENTS

| | | | | |
|---|---|---|---|---|
| 4,565,785 A | | 1/1986 | Gilbert et al. | 435/317 |
| 4,673,641 A | | 6/1987 | George et al. | 435/68 |
| 4,710,473 A | | 12/1987 | Morris | 435/320 |
| 4,738,921 A | | 4/1988 | Belagaje et al. | 435/68 |
| 4,795,706 A | | 1/1989 | Hsiung et al. | 435/172.3 |
| 5,342,763 A | | 8/1994 | Schwartz | 435/69.1 |
| 5,612,198 A | * | 3/1997 | Brierley et al. | |
| 5,639,635 A | | 6/1997 | Joly et al. | 435/69.7 |
| 5,789,199 A | * | 8/1998 | Joly et al. | 435/69.1 |
| 6,410,270 B1 | | 6/2002 | Strittmatter et al. | 435/696 |

FOREIGN PATENT DOCUMENTS

DE 19943919 3/2001

OTHER PUBLICATIONS

Flamez et al., Production in *Escherichia coli* of a functional murine and murine::human chimeric F (ab')2 fragment and mature antibody directed against human placental alkaline phosphatase, 1995, Journal of Biotechnology, vol. 42, pp. 133–143.*
Knorre et al., High cell density fermentation of recombinant *Escherichia coli* with computer–controlled optimal growth rate, 1991, Ann. NY. Acad. Sci., vol. 646, pp. 300–306.*
Skerra et al., Use of tetracycline promoter for the tightly regulated production of a murine antibody fragment in *Escherichia coli*, 1994, Gene, vol. 151, pp. 131–135.*
Gram et al., A novel approach for high level production of a recombinant human parathyroid hormone fragment in *Escherichia coli*, 1994, Bio/Technology, vol. 12, pp. 1017–1023.*
Cheng et al., "A Novel Feeding Strategy for Enhanced Plasmid Stability and Protein Production in Recombinant Yeast Fedbatch Fermentation." *Biotechnol. Bioeng.* 56:23–31 (1997).
Cruz et al., "Metabolic Shifts by Nutrient Manipulation in Continuous Cultures of BHK Cells." *Biotechnol. Bioeng.* 66:104–113 (1999).
Cruz et al., "Metabolically Optimised BHK Cell Fed–Batch Cultures." *J. Biotechnology.* 80:109–118 (2000).
Curless et al., Biotechnol. Prog. 1990, 6:149.
Ryan et al., Biotechnol. Prog. 1996, 12:596.
Yoon et al., Biotechnol. Prog. 1994, 43:995.
Villa–Komaroff, et al., Proc. Natl. Acad. Sci. USA 1978, 75:3727–373.
DeBoer et al., Proc. Natl. Acad. Sci. USA 1983, 80:21–25.
Sheibani, Prep. Biochem. Biotechnol. 1999, 29:77.
Gossen et al., Curr. Opin. Biotechnol. 1994, 5:516.
De Vos et al., Curr. Opin. Biotechnol. 1997, 8:547.
Chevalet et al., Biotechnol. Bioeng. 2000, 69:351.
Schroeckh et al., J. Biotechnol. 1999, 75:241.
Staijen et al., J. Bacteriol. 1999, 181:1610.
Newman and Fuqua, Gene 1999, 277:197.
Liu et al., Biotechniques 1998, 24:624.
Gallia and Khalili, Ongogene 1998, 16:1879.
Haldimann et al., J. Bacteriol. 1997, 179:5903.
Treuner–Lange et al., J. Bacteriol. 1997, 179:4501.
San et al., Ann. NY Acad. Sci. 1994, 721:268.
Bishai et al., J. Bacteriol. 1994, 176:2914.
Lama and Carrasco, Biochem. Biophys. Res. Commun. 1992, 188:972.
Nielson et al., Mol. Microbiol. 1991, 5:1961.
Alksne and Rasmussen, J. Bacteriol. 1997, 179:2006.
Everett et al., Microbiology 1995, 141:419.

(List continued on next page.)

*Primary Examiner*—David Guzo
*Assistant Examiner*—Daniel M. Sullivan
(74) *Attorney, Agent, or Firm*—Janet E. Hasak

(57) ABSTRACT

The invention provides a method for increasing product yield of a polypeptide of interest produced by recombinant host cells, where expression of the polypeptide by the recombinant host cells is regulated by an inducible system. More specifically, the method involves culturing the recombinant host cells under conditions of high metabolic and growth rate and then reducing the metabolic rate of the recombinant host cells at the time of induction of polypeptide expression. In particular, the invention provides a method of increasing product yield of an antibody, growth factor, or protease produced by a recombinant *E. coli* host cell regulated by an inducible system.

39 Claims, 4 Drawing Sheets

OTHER PUBLICATIONS

Curless et al., "Phosphate Glass as a Phosphate Source in High Cell Density *Escherichia coli* Fermentations" *Biotechnol. Prog.* 12:22–25 (1996).

Hellmuth et al, "Effects of growth rate on stablility and gene expression of recombinant plasmids during continuous and high cell density cultivation of *Escherichia coli* TG1" *Journal of Biotechnology* 32:289–298 (1994).

Lee and Chang,, "High Cell Density Culture of a Recombinant *Escherichia coli* Producing Penicillin Acylase in a Membrane Cell Recycle Fermentor" *Biotech and Bioengin* 36:330–337 (1990).

Lee, Sang Yup, "High cell–density culture of *Escherichia coli*" *Tibtech* 14:98–105 (Mar. 1996).

Vallejo et al., "Renaturation and purification of bone morphogenetic protein–2–produced as inclusion bodies in high–cell density cultures of recombinant *Escherichia coli* " 94:185–194 (2002).

Wilms et al., "High–Cell Density Fermentation for Production of L–N–Carbamoylase Using an Expression System Based on the *Escherichia coli* rhaBAD Promoter" *Biotech and Bioengin* 73:95–103 (2001).

* cited by examiner

METABOLIC RATE SHIFTS IN FERMENTATIONS EXPRESSING RECOMBINANT PROTEINS

This application claims priority under 35 U.S.C. §119(e) from U.S. Provisional Application Serial No. 60/245,962, filed Nov. 3, 2000.

FIELD OF THE INVENTION

The present invention relates to improvements in product yield from fermentation to produce recombinant proteins, particularly in prokaryotic and simple eukaryotic systems. More particularly, this invention greatly increases the yield of properly assembled proteins in large scale fermentations.

BACKGROUND OF THE INVENTION

The production of large quantities of relatively pure, biologically active polypeptides and proteins is important economically for the manufacture of human and animal pharmaceutical formulations, enzymes, and other speciality chemicals. Recombinant DNA techniques have become the method of choice to produce large quantities of exogenous proteins using bacteria and other host cells. The expression of proteins by recombinant DNA techniques for the production of cells or cell parts that function as biocatalysts is also an important application.

Producing recombinant protein involves transfecting host cells with DNA encoding the protein and growing the cells under conditions favoring expression of the recombinant protein. The prokaryote E. coli is favored as host because it can be made to produce recombinant proteins in high yields. Numerous U.S. patents on general bacterial expression of DNA encoding proteins exist, including U.S. Pat. No. 4,565,785 on a recombinant DNA molecule comprising a bacterial gene for an extracellular or periplasmic carrier protein and a non-bacterial gene; U.S. Pat. No. 4,673,641 on co-production of a foreign polypeptide with an aggregate-forming polypeptide; U.S. Pat. No. 4,738,921 on an expression vector with a trp promoter/operator and trp LE fusion with a polypeptide such as IGF-I; U.S. Pat. No. 4,795,706 on expression control sequences to include with a foreign protein; U.S. Pat. No. 4,710,473 on specific circular DNA plasmids such as those encoding IGF-I; U.S. Pat. No. 5,342,763 on improving expression in bacteria by manipulating oxygen delivery; and U.S. Pat. No. 5,639,635 on secretion of the expressed protein into the bacterial periplasm.

Recombinant proteins become less expensive if the fermentation yield improves. Yield depends upon the rate at which the recombinant protein is properly folded and assembled protein is formed and upon the length of time over which the protein is produced.

The recombinant protein expression rate is typically affected by the growth and metabolic rates of the cells. At higher growth rates, the rate at which a protein can be expressed when induced typically increases (Curless et al., Biotechnol. Prog. 1990, 6:149). However, upon induction, high protein expression rates may not always lead to high rates of formation of active, properly formed products. In other words, while the quantity of protein translated may be maximized, other factors may compromise the quality of the product, such as degradation of the protein by proteases or other detrimental post-translational modifications (Ryan et al., Biotechnol. Prog. 1996, 12:596; Yoon et al., Biotechnol. Prog. 1994, 43:995). Efficient fermentation requires balancing growth rate against yield of usable protein; compromises between these factors result in a decrease of the overall yield below its theoretical potential. Consequently, some intermediate growth rates may be more favorable for the production of high quantities of high quality product.

An added complication is that induction of recombinant protein expression essentially highjacks the cellular protein assembly process to make large quantities of a product with no benefit, and often with significant detriment, to the cell. In fact, for cases in which induction is triggered by phosphate depletion using the alkaline phosphatase promoter, growth rate is dramatically curtailed by the phosphate starvation itself. This effect does not affect the metabolic rate, however.

Thus, there is a need in the art to increase the yield of usable recombinant protein production. The present invention advantageously and unexpectedly addresses this need by permitting high levels of protein synthesis, assembly and folding. Because different factors may play critical roles in maximizing usable protein yield prior to induction during the growth phase of the culture, and post-induction, the independent control of these two factors can lead to improved yields of usable products, such as for the case of soluble, properly folded and assembled antibody fragments.

SUMMARY OF THE INVENTION

The invention provides a method for increasing product yield of a polypeptide of interest produced by recombinant host cells, where expression of the polypeptide by the recombinant host cells is regulated by an inducible system. More specifically, the method involves culturing the recombinant host cells under conditions of high metabolic and growth rate, then reducing the metabolic rate of the recombinant host cells at the time of induction of polypeptide expression.

In a specific embodiment the invention provides a method of increasing product yield of an antibody, growth factor, or protease produced by a recombinant E. coli host cell regulated by an inducible system.

In a further specific embodiment, the invention provides a method of increasing the yield of actively folded proteins having different structures, for example Fab'$_2$ versus Fab Fv antibody fragments, by selecting the time to initiate reduction in metabolic rate (the rate shift), the rate of adjustment (shift) of the metabolic rate, and the final metabolic rate. Adjusting these parameters of the invention enhances the yield of correctly folded proteins having different secondary and tertiary structures, interaction and refolding characteristics, size and contact area, and other factors that can affect protein assembly and function.

DETAILED DESCRIPTION

Figure 1:
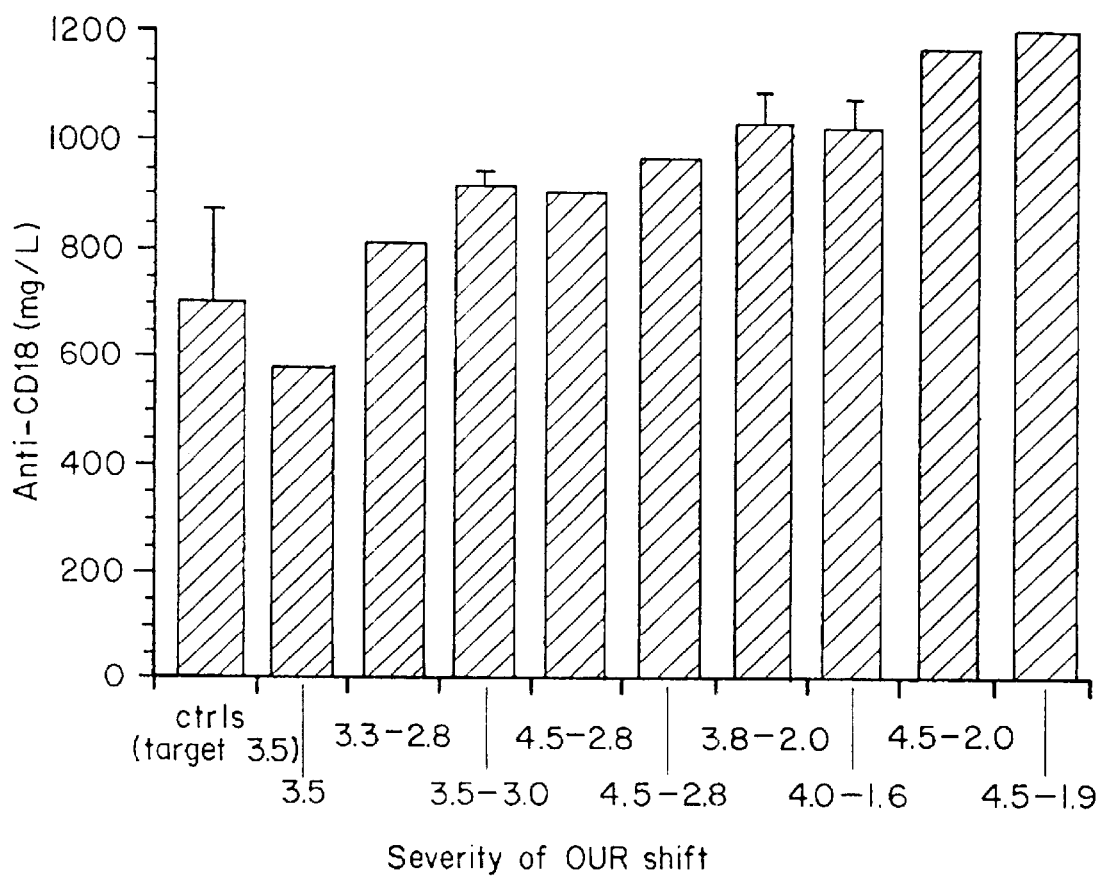
FIG. 1 shows anti-CD18 yield (titer) in a series of anti-CD18 Fab'$_2$ fermentations. X-axis: approximate oxygen uptake rate which reflects the severity of the oxygen use rate shift.

The present invention advantageously provides a method for increasing yield of a heterologous recombinant protein produced by recombinant host cells by first increasing the protein production capacity of the cells in culture by culturing the cells at a high growth rate, and then decreasing metabolic rate of the cells (rate shift) to permit proper folding or assembly of the heterologous protein. In a specific embodiment, implementing a high growth rate was found to extend the period of heterologous gene expression. In a further specific embodiment, the metabolic rate shift increases the yield of properly folded and, if appropriate, assembled protein. These features together increase fermentation efficiency.

The invention is based on observations in a number of $E.$ $coli$ fermentations producing anti-CD18 Fab'$_2$ and anti-VEGF Fab, that the deliberate down shifting of the cellular metabolic rate of the cells (by manipulating the oxygen transfer rate and correspondingly, the glucose feed rate in the fermentor) significantly improves product yields. In particular, growing the cells at a relatively high metabolic rate, and then dramatically shifting down the metabolic rate after the induction of antibody expression greatly improves yield. A substantial amount of data demonstrates that this approach extends the period of antibody fragment assembly, leading to significantly higher titers.

These experiments also established that for any given heterologous protein expression system, i.e., the nature of the protein and characteristic of the host, tuning the metabolic rate shift further increases useful protein yields. The tuning variables include the tuning of the metabolic rate shift, the step-down rate (rate of decrease in available oxygen or carbon/energy source, or both), and the final metabolic rate (available oxygen level, available carbon/energy source level or both).

Consequently, post-induction, the protein expression rate can be controlled by manipulating the metabolic rate, one common measure of which is the oxygen uptake rate of the cells in the fermentor. Metabolic rate control can be achieved by controlling the feeding of the primary carbon source, commonly glucose, often in conjunction with manipulation of fermentor parameters such as agitation rate and back pressure, to control the oxygen transfer rate to the cells. Conversely, metabolic rate control can be achieved by limiting the available oxygen, in conjunction with a reduction in the glucose feed rate. Similar trade-offs exist between protein synthesis rate and the rate of formation of usable product for controlling the metabolic rate post-induction as previously discussed for controlling growth rate pre-induction. For the case of maximizing the yield of antibody fragments, the rate and period of assembly of soluble, active product from the individual light-chain and heavy-chain polypeptides occurs at some favorable post-induction metabolic rate.

While data in the literature suggests that fermentations may have a favorable growth rate for protein production, the results in this application show that the shifting of metabolic rates in different phases of the fermentation provides a critical benefit. In other words, we see significantly improved product yields by shifting the metabolic rate compared to the titers obtained by running the fermentation at a previously favorable, constant metabolic rate. While all of the data to date has been obtained using fermentations producing antibody fragments in $E.$ $coli$, this approach applies to a variety of proteins, including growth hormone, expressed in other prokaryotic and simple eukaryotic systems.

As used herein, "reducing metabolic rate" or "shifting down metabolic rate" means altering the host cell culture conditions such that the host cells undergoing rapid growth and expansion reduce (or stop) growth and expansion. For the case of cells already in a reduced growth state, the rates of oxygen uptake and the corresponding rates of uptake of a carbon/energy source are reduced. Since, in the case of respiring cells, the metabolic rates are determined primarily by the rate at which the cell oxidizes the available carbon/energy source using the available oxygen, the metabolic rate can be reduced by limiting either of these two reactants. So reduction of metabolic rate can result from inter alia (1) reducing the amount of available oxygen in the cell culture (i.e., fermentation); (2) reducing the amount of available carbon/energy sources; or (3) reducing both.

The term "available oxygen" refers to oxygen that can be used by the cells. "Decreasing available oxygen" can be effected by decreasing the oxygen transfer rate to the culture, or decreasing the oxygen transfer by the cells or both. Often it is desirable to reduce the feed rate of glucose (or alternative carbon/energy source) correspondingly, and so the dissolved oxygen concentration may be decreased or not, depending on which reactant most directly limits respiration.

As used herein, the phrase "carbon/energy source" refers to a source of carbon and energy for the cells. Examples of such a source include glycerol, succinate, lactate, and sugars such as, e.g., glucose, lactose, sucrose, and fructose. The selection of the particular carbon/energy source to employ will depend mainly on the characteristics of the host cell. The preferred carbon/energy source for $E.$ $coli$ fermentation is glucose.

Thus, decreasing available carbon/energy sources can mean reducing the concentration or feed rate of the carbon/energy source, or reducing the rate of transfer to the host cells or uptake by the host cells of the carbon/energy source, or both.

As used herein "culturing the host cells under conditions of high metabolic and growth rate" means establishing the host cell culture conditions to favor growth. e.g., by providing unrestricted or relatively high feed rates of nutrients energy and oxygen, such that the cells have rapid growth and metabolic rates prior to reducing metabolic rate to increase "product yield". Under these conditions host cell doubling time decreases towards its minimum and host cell metabolism increases exponentially towards its maximum, potentially achieving either or both conditions. Measurement of metabolic And growth rates is easily determined using routine techniques, including but not limited to measurement of increases in cell number, measurement of increases in cell density (e.g., optical density), measurement of pH changes of the growth medium containing the cell, measurement of accumulated metabolites, measurement of heat production, measurement of electrical conductivity of the medium, measurement of nutrient feed rates, and measurement of oxygen uptake and carbon dioxide evolution rates.

As used herein, the term "product yield" refers to the quantity of useful recombinant protein produced by a fermentation system. Protein quantity is readily determined using routine techniques, including but not limited to chromatography, spectrometry gel electrophoresis, immunoassay, coomassie blue or silver staining, and the Lorry essay. Protein quality is further evaluated by comparing product to a standard in appropriate biophysical or activity assays, e.g., high performance liquid chromatography, spectroscopic analysis, or immunoassay. Activity assays can reveal properly folded or assembled functional protein. Thus, properly assembled antibody may bind antigen, preferably with similar affinity as a control antibody. A properly assembly growth factor, hormone, or cytokine will bind its cognate receptor and induce cell signaling, again in a manner comparable to that of wild-type growth factor, hormone, or cytokine. A properly refolded protease will cleave peptide bonds with similar specificity to that of a wild-type protease.

As used herein, "polypeptide of interest" refers generally to peptides and proteins having more than about 10 amino acids. The polypeptides may be endogenous to the bacterial host cell, or, preferably, may be exogenous to the host cell, such as yeast polypeptides, or more preferably, mammalian polypeptides. Examples of bacterial polypeptides include, e.g, alkaline phosphatase and beta-lactamase. Examples of mammalian polypeptides include molecules such as, e.g., renin, a growth hormone, including human growth hormone, des-N-methionyl human growth hormone, and bovine growth hormone; growth hormone releasing factor; parathyroid hormone; thyroid stimulating hormone; thyroxine; lipoproteins; alpha1-antitrypsin; insulin A-chain; insulin B-chain; proinsulin; follicle stimulating hormone; calcitonin; leutinizing hormone; glucagon; clotting factors such as factor VIIIC, factor IX, tissue factor and Von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hematopoietic growth factor; tumor necrosis factor-alpha and -beta; enkephalinase; a serum albumin such as human serum albumin; mullerian-inhibiting substance; relaxin A-chain; relaxin B-chain; pro-relaxin; mouse gonadotropin-associated peptide; a microbial protein, such as beta-lactanase; DNase; inhibin; activin; vascular endothelial growth factor; receptors for hormones or growth factors; integrin; thrombopoietin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-beta; platelet-derive growth factor (PDGF); fibroblast growth factor such as aFGF and bFGF; epidermal growth factor (EGF); transforming growth factor (TGF) such as TGF-alpha and TGF-beta, including TGF-beta1, TGF-beta2, TGF-beta3, TGF-beta4, or TGF-beta5; insulin-like growth factor-I and -II (IGF-I and IGF-II); insulin-like growth factor binding proteins; CD proteins such as CD-3, CD-4, CD-8, and CD-19; erythropoietin; osteoinductive factors; immunotoxins; a bone morphogenetic protein (BMP); somatotropins; interferons such as interferon-alpha, -beta, and -gamma; colony stimulating factors (CSFs), e.g., M-CSF, GM-CSF, and G-CSF; interleukins (ILs), e.g., IL-1 to IL-15; superoxide dismutase; T-cell receptors; surface membrane proteins; decay accelerating factor; viral antigens, such as, for example, a portion of the AIDS envelope; transport proteins; homing receptors; addressins; regulatory proteins; antibodies; and fragments of any of the above-listed polypeptides.

As used herein, the term "antibody" refers to full-length immunoglobins (IgA, IgD, IgE, IgG, IgM) and all isotypes thereof, humanized or chimeric antibodies, multispecific antibodies, CDR-modified antibodies, and antibody fragments thereof. Antibody fragments include Fab'$_2$, Fab, scFv single chain antibodies, and the like.

The preferred polypeptides of interest are those that are easily produced in bacterial cells with a minimum of proteolysis and a maximum in properly refolded or active material and need not be glycosylated for their intended utility. Examples of such mammalian polypeptides include antibodies (or fragments thereof), IGF-I, growth hormone, DNase, relaxin, growth hormone releasing factor, insulin, urokinase, immunotoxins, and antigens. Particularly preferred mammalian polypeptides include antibodies, IGF-I, and growth hormone.

A modified "host cell" is a cell in which a nucleic acid encoding the polypeptide of interest has been introduced. Alternatively the polypeptide of interest can be encoded by a gene that is part of the cell's genome, but for which regulatory sequences have been modified to provide for increased levels of expression.

Examples of host cells include, but are not limited to, bacterial organisms (bacteria), archaebacteria, simple single celled eukaryotes such as yeast and other fungi, plant cells, and animal cells. Suitable bacteria for this purpose include aerobic and facultative anaerobic bacteria, whether archaebacteria and eubacteria, especially eubacteria, and most preferably Enterobacteriaceae. Examples of useful bacteria include Escherichia, Enterobacter, Azotobacter, Erwinia, Bacillus, Pseudomonas, Klebsiella, Proteus, Salmonella, Serratia, Shigella, Rhizobia, Vitreoscilla, and Paracoccus. Suitable *E. coli* hosts include *E. coli* W3110 (ATCC 27,325), *E. coli* 294 (ATCC 31, 446), *E. coli* B, and *E. coli* X1776 (ATCC 31,537). These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *E. coli*, Serratia, or Salmonella species can be suitably used as the host when well known plasmids such as pBR322, pBR325, pACYC177, or pKN410 are used to supply the replicon. *E. coli* strain W3110 is a particularly preferred parent host because it is a common host strain for recombinant DNA product fermentations. Preferably, the host cell should secrete minimal amounts of proteolytic enzymes. For example, strain W3110 may be modified to effect a genetic mutation in the genes encoding proteins, with examples of such hosts including *E. coli* W3110 strain 1 A2, which has the complete genotype Δ fhuA; *E. coli* W3110 strain 9E4, which has the complete genotype Δ fhuA-ptr3; *E. coli* W3110 strain 27C7 (ATCC 55,244), which has the complete genotype Δ fhuA-ptr3 phoA-Δ-E15-Δ-(argF-lac) 169 ompT-Δ-degP41kan$^r$; *E. coli* W3110 strain 37D6, which has the complete genotype Δ fhuA-ptr3 phoA-Δ-E15-Δ-(argF-lac)169 ompT-Δ-degP41kan$^r$ rbs7-Δ-ilvG; *E. coli* W3110 strain 40B 4, which is strain 37D6 with a non-kanamycin resistant degP deletion mutation; and an *E. coli* strain having mutant periplasmic protease disclosed in U.S. Pat. No. 4,946,783 issued Aug. 7, 1990. Examples of mammalian cells are COS-1 or CHO cells, HeLa cells, 293T (human kidney cells), mouse primary myoblasts, and NIH 3T3 cells. Examples of yeast species are *S. cerevisiae, Candida albicans, Candida utilis*, and *Phaffia rhodozyma*. Other suitable host cells are insect cells such as SF-9 cells (*Spodoptera frugiperda*).

Host cells grow under amenable culture conditions, i.e., appropriate conditions of temperature (generally around 25–37° C.), pH (generally pH 7–8), humidity (generally about 100%), oxygen, and nutrient availability including carbon/energy sources. As described herein, availability of oxygen and an energy source determine host cell growth rate.

As used herein, "large-scale" fermentation refers to fermentation in a fermentor that is at least approximately 1000 liters in volumetric capacity, i e., working volume, leaving adequate room for headspace. "Small-scale" fermentation refers generally to fermentation in a fermentor that is no more than approximately 100 liters in volumetric capacity, preferably no more than approximately 10 liters.

Recombinant Host Cells

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. 1985); *Transcription And Translation* (B. D. Hames & S. J. Higgins, eds. 1984); *Animal Cell Culture* (R. I. Freshney, ed. 1986); *Immobilized Cells And Enzymes* (MRL Press, 1986); *A Practical Guide To Molecular Cloning* (B. Perbel, 1984); *Current Protocols in Molecular Biology*, (F. M. Ausubel et al. eds. 1994). *Escherichia coli* and Salmonella (Neidhardt et al., ASM Press, 1996), particularly describes recombinant technology in bacteria.

A "recombinant DNA molecule" is a DNA molecule that has undergone a molecular biological manipulation.

The polynucleotides herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g ., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

The term "gene", also called a "structural gene" means a DNA sequence that codes for or corresponds to a particular sequence of amino acids which comprise all or part of one or more proteins or enzymes, and may or may not include regulatory DNA sequences, such as promoter sequences, which determine for example the conditions under which the gene is expressed. Some genes, which are not structural genes, may be transcribed from DNA to RNA, but are not translated into a polypeptide sequence. Other genes may function as regulators of structural genes or as regulators of DNA transcription.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or secreted. The term "intracellular" means something that is inside a cell. The term "extracellular" means something that is outside a cell. A substance is "secreted" by a cell if it appears in significant measure outside the cell, from somewhere on or inside the cell.

The term "expression system" means a host cell and compatible vector under suitable conditions, e.g,. for the expression of a protein coded for by foreign DNA carried by the vector and introduced to the host cell. In a specific embodiment, the recombinant protein is expressed in *E coli* host cells.

The term "heterologous" refers to a combination of elements not naturally occurring. For example, heterologous DNA refers to DNA not naturally located in the cell, or in a chromosomal site of the cell. Preferably, the heterologous DNA includes a gene foreign to the cell. A heterologous expression regulatory element is such an element operatively associated with a different gene than the one it is operatively associated with in nature. In the context of the present invention, a gene encoding a protein of interest in heterologous to the vector DNA in which it is inserted for cloning or expression, and it is heterologous to a host cell containing such a vector, in which it is expressed, e.g., an *E. coli* cell.

The term "transfection" means the introduction of a foreign nucleic acid into a cell. The term "transformation" means the introduction of a "foreign" (i.e., extrinsic or extracellular) gene, DNA or RNA sequence to a host cell, so that the host cell will replicate the DNA and express the introduced gene or sequence to produce a desired substance, typically a protein or enzyme coded by the introduced gene or sequence. The introduced gene or sequence may also be called a "cloned" or "foreign" gene or sequence, and may include regulatory or control sequences, such as start, stop, promoter, signal, secretion, or other sequences used by a cell's genetic machinery. The gene or sequence may include nonfunctional sequences or sequences with no known function. DNA may be introduced either as an extrachromosomal element or by chromosomal integration, and a host cell tat receives and expresses introduced DNA or RNA has been "transformed" and is a "transformant" or a "clone." The DNA or RNA introduced to a host cell can come from any source, including cells of the same genus or species as the host cell, or cells of a different genus or species.

Depending on the host cell used, transformation is done using standard techniques appropriate to such cells. The calcium treatment employing calcium chloride, as described in section 1.82 of Sambrook et al., supra, is generally used for bacterial cells that contain substantial cell-wall barriers. Another method for transformation employs polyethylene glycol/DMSO, as described in Chung and Miller (Nucleic Acids Res. 1988, 16:3580). Yet another method is the use of the technique termed electroporation.

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc.; they are discussed in greater detail below.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and that can readily be introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence that initiates, regulates, or otherwise mediates or controls the expression of the coding DNA. Promoter DNA and coding DNA may be from the same gene or from different genes, and may be from the same or different organisms.

A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

A wide variety of host/expression vector combinations (i.e., expression systems) may be employed in expressing the proteins of interest. Useful expression vectors, for example, may consist of segments of chromosomal, non-chromosomal and synthetic DNA sequences. Suitable vectors include known bacterial plasmids, e.g., $E.$ $coli$ plasmids col E1, pCR1, pBR322, pMal-C2, pET, pGEX (Smith et al., Gene 67:31–40, 1988), pMB9 and their derivatives, plasmids such as RP4; phage DNAS, e.g., the numerous derivatives of phage 1, e.g., NM989, and other phage DNA, e.g., M13 and filamentous single stranded phage DNA; yeast plasmids such as the 2 m plasmid or derivatives thereof; vectors derived from combinations of plasmids and phage DNAs, such as plasmids that have been modified to employ phage DNA or other expression control sequences; and the like.

Yeast expression systems can also be used according to the invention to express any protein of interest. For example, the non-fusion pYES2 vector (XbaI, SphI, ShoI, NotI, GstXI, EcoRI, BstXI, BamH1, SacI, Kpn1, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with Pro-Bond resin and cleaved with enterokinase; Invitrogen), to mention just two, can be employed according to the invention.

The host cells can inherently also harbor the polypeptide of interest. For example, alkaline phosphatase is a protein that is homologous to $E.$ $coli$ and can be induced without any further transfection of the cell with vector DNA. For heterologous polypeptides such as, e.g., antibody and growth hormone, the heterologous nucleic acid (e.g., cDNA) is suitably inserted into a replicable vector for expression in the culture medium under the control of a suitable promoter. As noted above, many vectors are available for this purpose, and selection of the appropriate vector will depend mainly on the size of the nucleic acid to be inserted into the vector and the particular host cell to be transformed with the vector. Each vector contains various components depending on its f unction (amplification of DNA or expression of DNA) and the particular host cell with which it is compatible. The vector components for bacterial transformation generally include, but are not limited to, one or more of the following: a signal sequence, an origin of replication, one or more marker genes, and a promoter.

The DNA encoding the polypeptide of interest herein may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, penicillinase, lpp, or heat-stable enterotoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria. The origin of replication from the plasmid pBR322 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline; (b) complement auxotrophic deficiencies; or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen.

The expression vector for producing a heterologous polypeptide also contains an inducible promoter that is recognized by the host organism and is operably linked to the nucleic acid encoding the polypeptide of interest. Promoters suitable for use with bacterial hosts include the beta-lactamase and lactose promoter systems (Chang et al., Nature 1978, 275:615; Goeddel et al., Nature 1979, 281:544), alkaline phosphatase, a tryptophan (trp) promoter system (Goeddel, Nucleic Acids Res. 1980, 8:4057 and EPO 36,776) and hybrid promoters such as the tac promoter (deBoer et al., Proc. Natl. Acad. Sci. USA 1983, 80:21–25). However, other known bacterial promoters are suitable. Their nucleotide sequences have been published, thereby enabling a skilled worker operably to ligate them to DNA encoding the polypeptide of interest (Siebenlist et al., Cell 1980, 20:269) using linkers or adaptors to supply any required restriction sites. Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

An "inducible promoter" or "regulated promoter" is a promoter that regulates expression in response to a stimulus. The promoter may be bound by a transcription regulatory protein, e.g., a repressor or an activator, which represses or activates gene expression, respectively. The repressor or activator protein in turn is responsive to the stimulus, such as the presence or absence of a nutrient, such as lactose, a nutrient such as phosphate, a toxin, such as a heavy metal, acidic pH, increased temperature, or some other environmental signal.

A coding sequence is "under the control of" or "operatively associated with" transcriptional and translational control sequences in a cell when RNA polymerase transcribes the coding sequence into mRNA, which is then trans-RNA spliced (if it contains introns) and translated into the protein encoded by the coding sequence.

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) or other strains, and successful transformants are selected by ampicillin or tetracycline resistance where appropriate. Plasmids from the transformants are prepared, analyzed by restriction endonuclease digestion, and/or sequenced by the method of Sanger et al., Proc. Natl. Acad. Sci. USA 1977, 74:5463–5467 or Messing et al., Nucleic Acids Res. 1981, 9:309), or by the method of Maxam et al. (Methods in Enzymology 1980, 65:499).

Host cells are transformed with the above-described expression vectors of this invention and cultured in conventional nutrient media modified as appropriate for the promoter utilized.

Inducible Expression Systems

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., Gene 1977, 2:95). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

Thus, expression of the polypeptide of interest may be controlled by any inducible promoter/enhancer element known in the art, but these regulatory elements must be functional in the host selected for expression. Promoters that may be used to control gene expression include, but are not limited to, prokaryotic expression promoters such as the beta-lactamase promoter (Villa-Komaroff, et al., Proc. Natl. Acad. Sci. USA 1978, 75:3727–3731), or the tac promoter (DeBoer, et al., Proc. Natl. Acad. Sci. USA 1983, 80:21–25; see also Sheibani, Prep. Biochem. Biotechnol. 1999, 29:77; "Useful proteins from recombinant bacteria" in Scientific American, 242:74–94, 1980; Gossen et al., Curr. Opin. Biotechnol. 1994, 5:516). In a specific embodiment, a phoA promoter provides for regulated expression. Expression systems have been described for industrial Gram-positive bacteria, such as Bacillus, Clostridium, Lactococcus, Lactobacillus, Staphylococcus and Streptococcus based primarily on the capacity of these bacteria to utilize specific sugars or to secrete autoinducing peptides that are involved in quorum sensing (de Vos et al., Curr. Opin. Biotechnol. 1997, 8:547), particularly for lactic acid bacteria (de Vos, Curr. Opin. Microbiol. 1999, 2:289; Djordjevic and Klaenhammer, Mol. Biotechnol. 1998, 9:127). Other expression systems include, but are by no means limited to, the tryptophan promoter (Chevalet et al., Biotechnol. Bioeng. 2000, 69:351), the *E. coli* Ntr-system (Schroeckh et al., J. Biotechnol. 1999, 75:241); the PalkBFGHJKL promoter (Staijen et al., J. Bacteriol. 1999, 181:1610); the *E. coli* araBAD promoter/araC regulator system (Newman and Fuqua, Gene 1999, 227:197); tetracycline-regulated systems (Liu et al., Biotechniques 1998, 24: 624; Gallia and Khalili, Oncogene 1998, 16:1879); the VanS-VanR two-component regulatory system (Haldimann et al., J. Bacteriol. 1997, 179:5903); a potassium-regulated system (Treuner-Lange et al., J. Bacteriol. 1997, 179:4501); a pH-inducible system (San et al., Ann. NY Acad. Sci. 1994, 721:268), a peroxide/ascorbate-inducible system (Bishai et al., J. Bacteriol. 1994, 176:2914); systems based on the T7 promoter (see Lama and Carrasco, Biochem. Biophys. Res. Commun. 1992, 188:972); antibiotic-inducible systems (see Nielsen et al., Mol. Microbiol. 1991, 5:1961); and other regulated systems (see Alksne and Rasmussen, J. Bacteriol. 1997, 179:2006; Everett et al., Microbiology 1995, 141:419).

Inducible promoter elements from yeast or other fungi such as the Gal 4 promoter, the ADC (alcohol dehydrogenase) promoter, PGK (phosphoglycerol kinase) promoter, alkaline phosphatase promoter are also well known.

Fermentations

Various larger-scale fed-batch fermentations are available for production of recombinant proteins. Larger fermentations have at least 1000 liters of capacity, preferably about 1000 to 100,000 liters of capacity, i.e., working volume, leaving adequate room for headspace. These fermentors use agitator impellers or other suitable means to distribute oxygen and nutrients, especially glucose (the preferred carbon/energy source). Small-scale fermentation refers generally to fermentation in a fermentor that is no more than approximately 100 liters in volumetric capacity, preferably no more than approximately 10 liters.

Host cells used to produce the polypeptide of interest of this invention are cultured in suitable media in which the promoter can be constitutively or artificially induced as described generally, e.g, in Sambrook et al., supra. Examples of suitable media are given below in the example section.

Any necessary supplements besides carbon, nitrogen, and inorganic phosphate sources may also be included at appropriate concentrations introduced alone or as a mixture with another supplement or medium such as a complex nitrogen source.

Initially, prior to expression of the polypeptide of interest, the host cells inoculated into the fermentor are grown under favorable growth conditions, e.g., with all of the available oxygen and carbon/energy sources (or, preferably, source), along with essential nutrients and pH control, necessary for logarithmic growth. In accordance with the invention, these conditions are maintained, e.g., by feeding concentrated glucose at a rate that controls dissolved oxygen content at a set point, until the host cells expand in culture to the desired number or cell density.

After reaching target cell density, two manipulations of the fermentation occur. The first is to provide the signal to induce expression of the polypeptide of interest, e.g., by depleting phosphate levels as exemplified infra.

The second manipulation (which can result from the first) is to downshift or reduce the host cell metabolic rate. Since during logarithmic growth the metabolic rate is directly proportional to availability of oxygen and a carbon/energy source, reducing the levels of available oxygen or carbon/energy sources, or both, will reduce metabolic rate. Manipulation of fermentor operating parameters, such as agitation rate or back pressure, as well as reducing $O_2$ pressure, modulates available oxygen levels. Reducing concentration or delivery rate, or both, of the carbon/energy source(s) has similar effect. Furthermore, depending on the nature of the expression system, induction of expression can lead to a dramatic decrease in metabolic rate. Finally, upon reaching maximum cell density, growth stops or the rate decreases dramatically.

As discussed above, reduction in host cell metabolic rate results in more controlled expression of the polypeptide of interest, which permits folding and protein assembly to occur.

Gene expression may be measured in a sample directly, for example, by conventional Northern blotting to quantitate the transcription of mRNA (Thomas, Proc. Natl. Acad. Sci. USA 1980, 77: 5201–5205). Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like.

The polypeptide of interest preferably is recovered from the periplasm or culture medium as a secreted polypeptide, although it also may be recovered from host cell lysates when directly expressed without a secretory signal. Alternatively, the cells or portions thereof may be used as biocatalysts or for other functions without substantial purification.

It is often preferred to purify the polypeptide of interest from recombinant cell proteins or polypeptides to obtain preparations that are substantially homogeneous as to the polypeptide of interest. As a first step, the culture medium or lysate is centrifuged to remove particulate cell debris. The membrane and soluble protein fractions may then be separated if necessary. The polypeptide may then be purified from the soluble protein fraction and from the membrane fraction of the culture lysate, depending on whether the polypeptide is membrane bound, is soluble, or is present in an aggregated form. The polypeptide thereafter is solubilized and folded, if necessary, and is purified from contaminant soluble proteins and polypeptides, with the following procedures being exemplary of suitable purification procedures: fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; and gel filtration using, for example, Sephadex G-75.

EXAMPLES

The following examples illustrate without limiting the invention.

Example 1

Anti-CD18 Fermentation

Materials and Methods

Fermentation

The host used in these fermentations was a derivative of E. coli W3110, designated 49A5. The complete genotype of 49A5 is W3110 ΔfhuA phoAΔAE15Δ(argF-lac)169deoC degP41 (ΔPstI-Kan$^r$) IN (rrnD-rrnE)1 ilvG2096(Val$^r$) ΔfucPΔmalE. The plasmid, pS1130, contains the genes from the light-chain fragment of anti-CD18 and a fragment of the heavy chain with a C-terminal leucine-zipper, both behind the phoA promoter and both preceded by a STII signal sequence. Consequently, upon induction of expression, the light-chain and heavy-chain fragments were synthesized and secreted into the periplasm where some fraction of the individual peptides fold and assemble to form an Fab'$_2$ with leucine zippers on the heavy chains.

For each 10-liter fermentation, a single vial containing 1.5 ml of culture in 10–15% DMSO was thawed into a 1L shake flask containing 500 ml of LB medium supplemented with 0.5 ml of tetracycline solution (5 mg/ml) and 2.5 ml IM sodium phosphate solution. This seed culture was grown for approximately 16 hours at 30° C. and was then used to inoculate a 10-liter fermentor.

The fermentor initially contained approximately 4.7 liters of medium containing approximately 3.5 g of glucose, 75 ml of 1M magnesium sulfate, 8 ml of a trace element solution (27 g/L ferric chloride hexahydrate, 8 g/L zinc sulphate heptahydrate, 7 g/L cobalt chloride hexahydrate, 7 g/L sodium molybdate, 8 g /L cupric sulfate pentahydrate, 2 g /L boric acid, 5 g/L manganese sulfate monohydrate, 10% hydrochloric acid), 8 ml of a 2.7% ferric chloride solution, 15 ml of a tetracycline solution (5 mg/ml in ethanol), 7.5 ml of Fermax Adjuvant 27 (or some equivalent anti-foaming agent), 1 bag of HCD salts (19.5 g potassium phosphate dibasic, 9.75 g sodium phosphate monobasic dihydrate, 37.5 g ammonium sulfate, 7.5 g sodium citrate dihydrate, 11.3 g potassium phosphate monobasic) and 150 g of NZ Amine A (a protein hydrolysate). Fermentations were performed at 30° C. with 10 slpm of air flow and were controlled at a pH of 7.0±0.2 (although occasional excursions beyond this range occurred in some cases). The fermentor back pressure and agitation rate were varied to manipulate the oxygen transfer rate in the fermentor and, consequently, control the cellular respiration rate.

Following inoculation of the fermentor with the cell-containing medium from the shake flask, the culture was grown in the fermentor to high cell densities using a computer-based algorithm to feed a concentrated glucose solution to the fermentor. Ammonium hydroxide (58% solution) and sulfuric acid (24% solution) were also fed to the fermentor as needed to control pH. Further additions of anti-foam were also used in some cases to control foaming. When the culture reached a cell density of approximately 40 $OD_{550}$, an additional 75 ml of 1M magnesium sulfate was added to the fermentor. Additionally, a concentrated salt feed (10 g/L ammonium sulfate, 26 g/L potassium phosphate dibasic, 13 g/L sodium phosphate monobasic dihydrate, 2 g/L sodium citrate dihydrate, 15 g/L potassium phoshate monobasic, 8 ml/L 2.7% ferric chloride, 8 ml/L trace elements solution) was started at a rate of 1.9 ml/min when the culture reached approximately 20 $OD_{550}$ and continued until approximately 940 ml were added to the fermentation. Fermentations were typically continued for 72–80 hours.

During the fermentation, once the dissolved oxygen setpoint for the fermentation was reached, the concentrated glucose solution was fed based on the dissolved oxygen probe signal in order to control the dissolved oxygen concentration at the setpoint without excess glucose feeding. Consequently, in this control scheme, manipulations of fermentor operating parameters such as the agitation rate or back pressure, which affect the oxygen transfer capacity in the fermentation, correspondingly manipulate the oxygen uptake rate or metabolic rate of the cells.

A mass spectrometer was used to monitor the composition of the off-gas from the fermentations and enable the calculation of the oxygen uptake and carbon dioxide evolution rates in the fermentations.

Product Assays

To assess the quantity of antibody product in the fermentations, a number of assays were used. To measure assembled anti-CD18 $Fab'_2$-leucine zipper, a cation exchange HPLC (high performance liquid chromatography) assay was used. To prepare cell samples for this assay, fermentation broth was first diluted in phosphate-buffered saline to a concentration of 20 $OD_{550}$. One ml of this diluted broth was then centrifuged for 15 minutes at approximately 15,000×g and the remaining supernatant was discarded, leaving a cell pellet for the HPLC analysis. This pellet was then frozen at −20° C. to −70° C. until needed for the assay. The frozen pellets were resuspended in a lysis buffer containing 500 $\mu$l of 100 mM (or 200 mM) TRIS buffer at pH 8, 20 $\mu$l of 6 mg/ml lysozyme in water (freshly prepared), and 10 $\mu$l of 100 mM EDTA. The samples were sonicated for 10 pulses, and then incubated typically on ice for at least thirty minutes prior to further analysis. In some cases, a second round of sonication may then be performed. The samples were then centrifuged again for fifteen minutes at approximately 15,000×g to obtain the soluble fraction of the lysate (in the supernatant). Samples were diluted at least 1:1 and 250 $\mu$l were loaded onto a CsX column on a Hewlett-Packard 1090 HPLC system. Samples were eluted using a gradient of 5 to 50 mM sodium phosphate (pH 7.0) over fourteen minutes, and peaks were monitored using UV absorbance at 278 nm. The peak containing anti-CD18 Fab'2-leucine zipper was identified and quantified by comparison with purified standards.

Results

A series of anti-CD18 $Fab'_2$ fermentations were run in which varying oxygen uptake rate profiles were used (FIG. 1). The control used a constant with a previously favorable oxygen uptake rate. The x-axis shows the approximate oxygen uptake rates during the growth phase and at the end of the fermentation. The case with the single number of 3.5 represents an unshifted control run at approximately 3.5 mmol/1/min $O_2$. The controls represent an average of nine fermentations run using similar conditions to the shifted cases with the exception that no attempts were made to shift the OUR resulting in roughly constant OUR's of 3.5.

Figure 2:
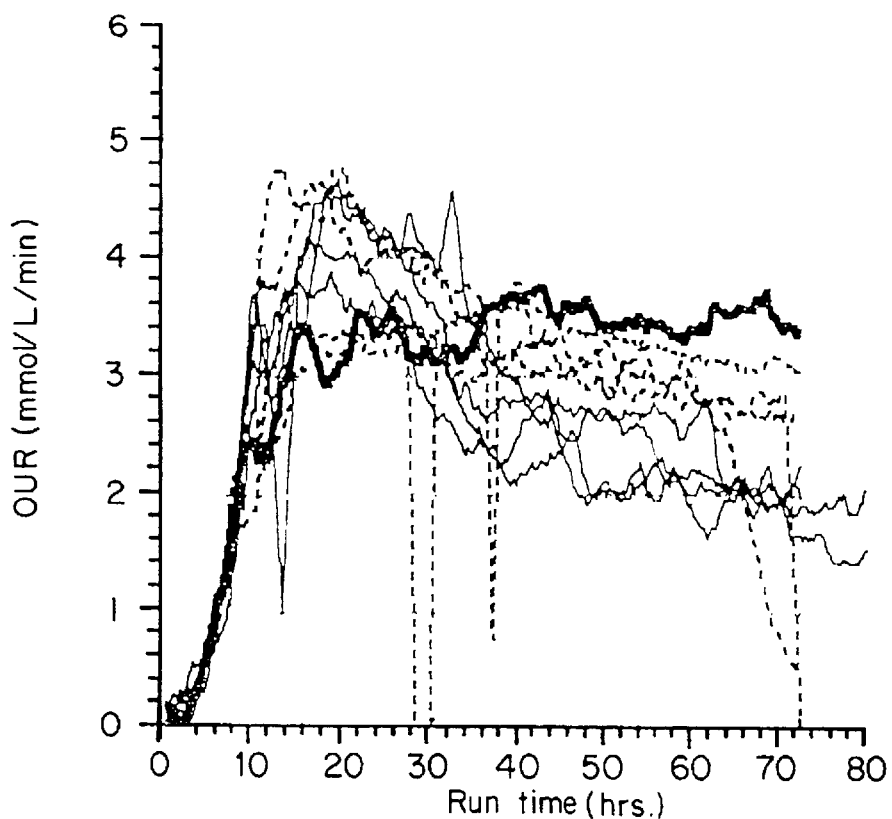
FIG. 2 shows actual oxygen uptake rate profile from the fermentations in FIG. 1. Titers exceeding 1000 mg/L are represented by a thin solid line (⎯⎯); titers between 800–900 mg/L are represented by a dotted line (-----); and the unshifted control (~600 mg/L) is represented by a heavy solid line (⎯⎯).

The actual oxygen uptake rate profiles from the fermentations shown in FIG. 1 are displayed and are grouped according to titer (FIG. 2). The runs in which the titer exceeded 1000 mg/L are shown in four runs (#1–4) recorded with a thin solid line, the runs in which the titer was between 800–900 mg/L are shown in four runs (#5–8) recorded with a dotted line, and the unshifted control run is shown in the run (#9) recorded with a heavy solid line. These results strongly support the hypothesis that increased down-shifts of the oxygen uptake rates significantly increase the fermentation yield of anti-CD18 Fab'2.

Figure 3:
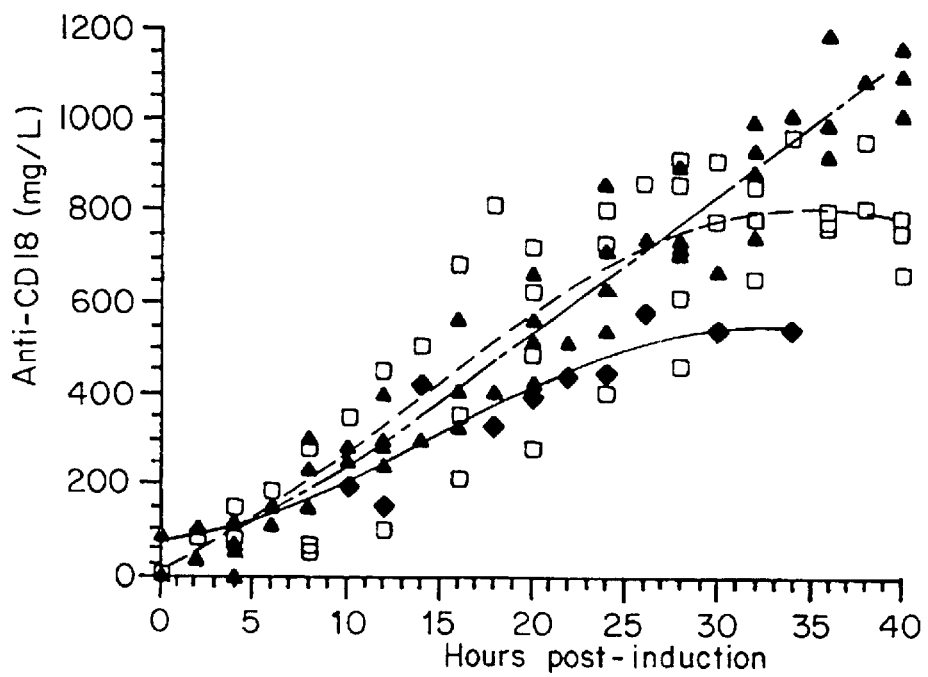
FIG. 3 shows the titer results for quantitating antibody production of the various runs as a function of fermentation time. A less severe shift is represented by squares (---□---), a more severe shift is represented by triangles (▲---) and the control is represented by diamonds (♦).

To further investigate the cause of this effect, the titer assay results for these various runs are shown as a function of fermentation time (FIG. 3). These results suggest that in the cases with the largest OUR shifts, anti-CD18 yield is increased as a result of an extended period of product formation.

Example 2

Anti-VEGF Fermentation

Materials and Methods

Fermentation

The organism used for these fermentations was 43H1 W3110 ΔfhuA phoAΔE15 Δ(argF-lac)169ptrA ΔompT degP41 (ΔPstI-Kan$^r$) IN (rrnD-rrnE)1 ilvG209(Val$^r$) prc-::kan prc suppressor. The plasmid used in these runs was Y0317tet20 and confers resistance to ampicillin and tetracycline. Anti-VEGF Fab was expressed from the phoA promoter. For the standard protocol, the fermenter conditions did not change with time. For the oxygen use rate (OUR) shifted runs, the agitation and back pressure were gradually decreased from 1000 RPM and 1.0 bar to 600 RPM and 0.3 bar respectively.

The standard and "OUR" fermentation protocols are summarized in Table 1.

TABLE 1

OUR Shift and Standard Protocols

| Parameter | Standard | OUR Shifted |
|---|---|---|
| Temperature | 30° C. | 30° C. |
| Airflow | 20 L/min | 20 L/min |
| Back pressure | 1.0 bar constant | 1.0 start decreasing to 0.3 bar |
| Agitation Rate | constant | 1000 RPM decreasing to 600 |
| Salt Feed | 650 RPM constant high cell density salts* | high cell density salts* with yeast extract (100 g) |

*High cell density salts is a feed consisting of inorganic salts yielding between 200–300 $OD_{550}$ units. Extra yeast extract without the OUR shift protocol decreases the yield of the product.

Product Sample Preparation and Product Assay

One-milliliter samples of fermentation broth were taken every two hours and frozen on dry ice. Samples were stored long term at −20° C. The samples were subsequently thawed and diluted 6× into extraction buffer (10 mM TrisCl, pH6.8, 1 mM EDTA, 0.2 mg/ml lysozyme, and 5 mM iodoacetamide) and vortexed. After ten minutes on ice, 1/100 volume of 1 M $MgSO_4$ and 1/100 volume of 2 mg/ml DNAse were added and the samples vortexed again. After another ten-minute incubation on ice, the samples were sonicated for ten seconds (Branson sonifier, microtip probe, setting 4, pulsed) and placed back on ice. Sonication was repeated for a total of two rounds. The samples were then centrifuged for twenty minutes at 4° C. at 16,000×g. The resulting supernatants were then analyzed by affinity chromatography using VEGF immobilized on an HPLC resin (Poros AL). The VEGF column was loaded and equilibrated in phosphate-buffered saline and the product eluted in 12 mM HCl with 150 mM NaCl. The product was quantitated by measuring the $A_{280}$ of the samples and comparing to a standard curve generated by spiking purified anti-VEGF into fermentation broth containing either anti-CD18 or Apo2L.

Results

Figure 4A:
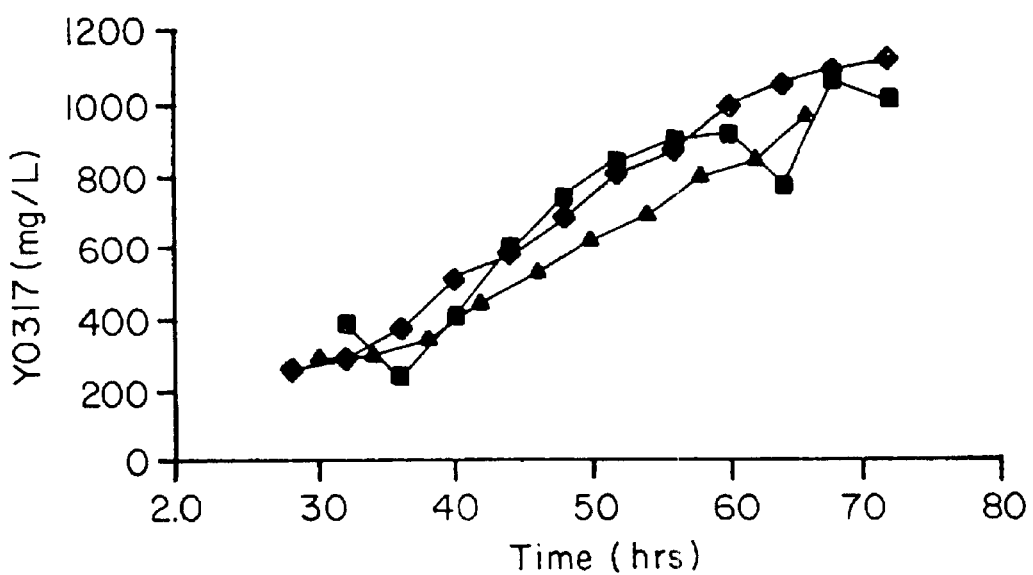
FIGS. 4A and 4B show titer profiles for a series of anti-VEGF fermentations or without (B) oxygen use rate (OUR) shifts. The graphs each present data from three runs. Run 1 is represented by diamonds (♦), Run 2 is represented by squares (■) and Run 3 is represented by triangles (▲).
Figure 4B:
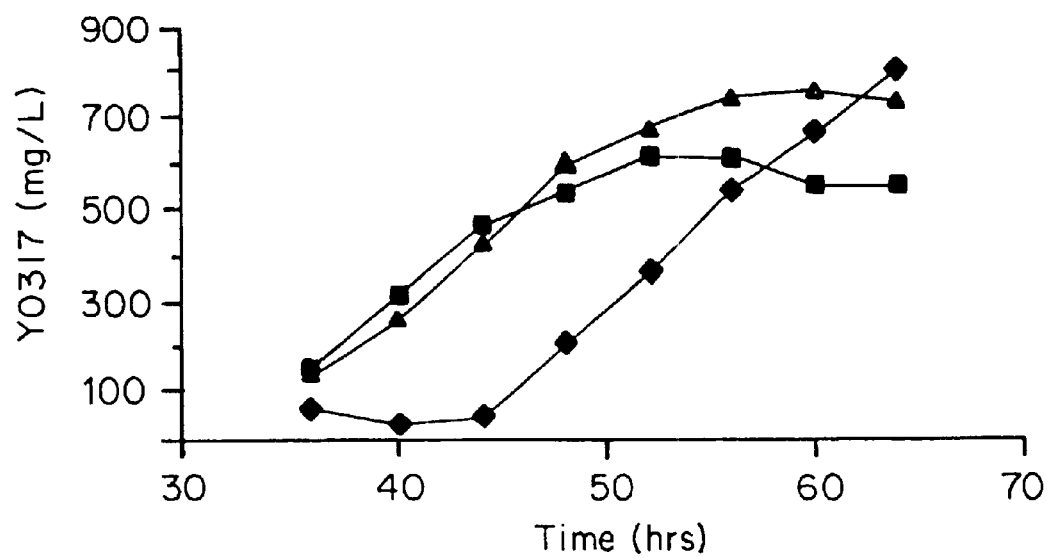

Observations for anti-VEGF Fab fermentations were similar to those with anti-CD18 $Fab'_2$. Titer profiles for a series of anti-VEGF fermentations with and without OUR shifts are shown in FIG. 4. These data demonstrate a statistically significant improvement in titer as a result of the OUR shifts compared to the standard protocol (See Table 2).

TABLE 2

Titer profiles for OUR Shifts vs Standard Protocols

|  | OUR Shift (mg/L) | Standard (mg/L) |
|---|---|---|
| RUN 1 | 1107.6 | 805.4 |
| RUN 2 | 999.5 | 552.5 |
| RUN 3 | 956.4 | 736.9 |
| Average | 1021.2 | 698.3 |
| Standard Deviation | 77.9 | 130.8 |
| t-test | 0.01 | |

Figure 5A:
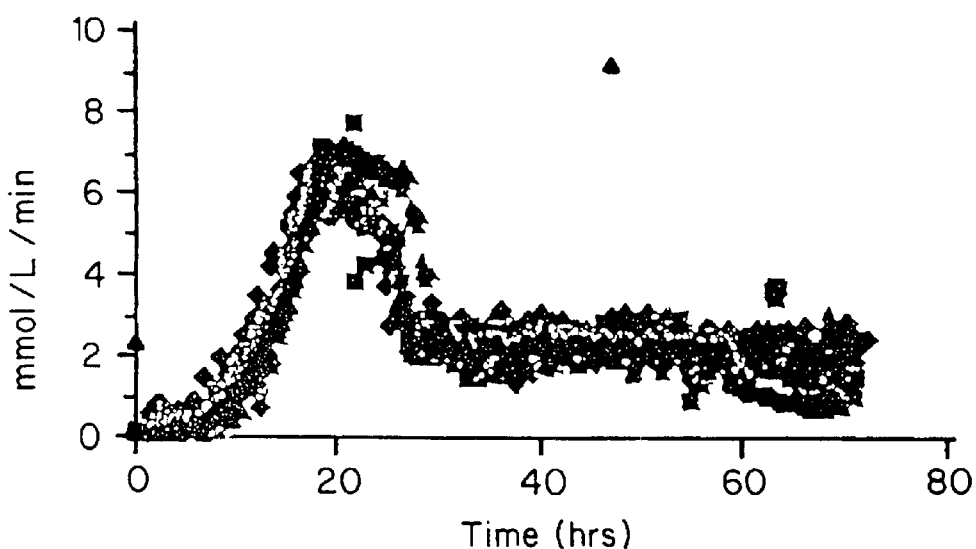
FIGS. 5A and 5B show OUR profiles for the runs in FIG. 4. Run 1 is represented by diamonds (♦), Run 2 is represented by squares (■) and Run 3 is represented by triangles (▲).
Figure 5B:
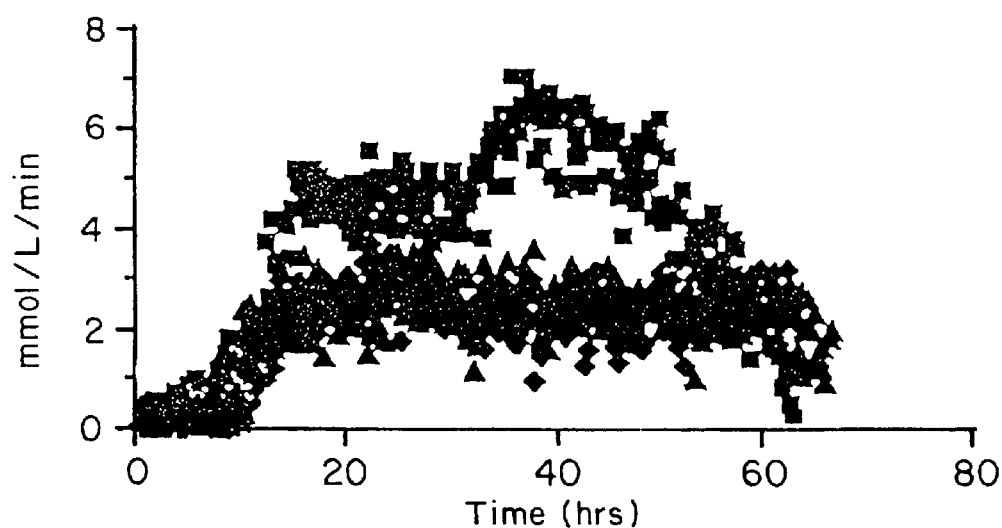

The corresponding OUR profiles for these runs are shown in FIG. 5.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for increasing product yield of a properly folded polypeptide of interest produced by recombinant host cells, wherein expression of the polypelptide by the recombinant host cells is regulated by an inducible system, which method comprises
    (a) culturing the recombinant host cells under conditions of high metabolic and growth rate; and
    (b) reducing the metabolic rate of the cultured recombinant host cells at the time of induction of polypeptide expression, wherein reducing the metabolic rate comprises reducing the feed rate of a carbon/energy source, or reducing the amount of available oxygen, or both, and wherein the reduction in metabolic rate results in increased yield of properly folded polypeptide.

2. The method according to claim 1, wherein reducing the metabolic rate comprises decreasing available oxygen to the host cells.

3. The method according to claim 1, wherein reducing the metabolic rate comprises decreasing available carbon/energy sources to the host cells.

4. The method according to claim 3, wherein the carbon/energy source is glucose.

5. The method according to claim 1, wherein reducing the metabolic rate comprises decreasing both the oxygen transfer rate and available carbon/energy source to the host cells.

6. The method according to claim 1, wherein the metabolic rate is reduced by about half in step (b).

7. The method according to claim 1, which comprises growing the cells to maximum density in step (a).

8. The method according to claim 7, wherein the metabolic rate is reduced by about half in step (b).

9. The method according to claim 1, wherein the recombinant host cell is a bacterial cell selected from the group consisting of E. coli and Salmonella.

10. The method according to claim 1, wherein the inducible system is a phosphate depletion inducible system.

11. The method according to claim 1, wherein the polypeptide is assembled in the host cell.

12. The method according to claim 9, wherein the polypeptide is secreted into the periplasm of the host cell.

13. The method according to claim 1, wherein the polypeptide is an antibody.

14. The method according to claim 1, wherein the polypeptide is selected from the group consisting of an $Fab'_2$ antibody and an Fab antibody or other form of antibody.

15. The method according to claim 1, wherein the metabolic and growth rate of the host cells is maximized in step (a).

16. A method of increasing product yield of a properly folded antibody, growth factor, or mammalian protease produced by a recombinant E. coli host cell, wherein expression of the antibody, growth factor, or protease is regulated by an inducible system, which method comprises
    (a) culturing host cells under conditions of high metabolic and growth rate; and
    (b) reducing metabolic rate of the recombinant host cells at the time of induction of antibody, growth factor, or protease expression.

17. The method according to claim 16, wherein the antibody is an Fab'$_2$ antibody.

18. The method according to claim 16, wherein the antibody is an Fab antibody.

19. The method according to claim 16, wherein reducing the metabolic rate comprises decreasing available oxygen to the host cells.

20. The method according to claim 16, wherein reducing the metabolic rate comprises decreasing available carbon/energy sources to the host cells.

21. The method according to claim 19, wherein the carbon/energy source is glucose.

22. The method according to claim 16, wherein the metabolic rate is reduced by about half in step (b).

23. The method according to claim 16, wherein the inducible system is a phosphate depletion inducible system.

24. The method according to claim 16, wherein the metabolic and growth rate of the host cells is maximized in step (a).

25. A method for increasing product yield of a properly folded mammalian polypeptide of interest produced by recombinant host cells, wherein expression of the polypeptide by the recombinant host cells is regulated by an inducible system, which method comprises (a) culturing the recombinant host cells under conditions of high metabolic and growth rate; and (b) reducing metabolic rate of the recombinant host cells at the time of induction of polypeptide expression.

26. The method according to claim 25, wherein reducing the metabolic rate comprises decreasing available oxygen to the host cells.

27. The method according to claim 25, wherein reducing the metabolic rate comprises decreasing available carbon/energy sources to the host cells.

28. The method according to claim 25, wherein the carbon/energy source is glucose.

29. The method according to claim 25, wherein reducing the metabolic rate comprises decreasing both the oxygen transfer rate and available carbon/energy source to the host cells.

30. The method according to claim 25, wherein the metabolic rate is reduced by about half in step (b).

31. The method according to claim 25, which comprises growing the cells to maximum density in step (a).

32. The method according to claim 31, wherein the metabolic rate is reduced by about half in step (b).

33. The method according to claim 25, wherein the recombinant host cell is a bacterial cell selected from the group consisting of *E. coli* and Salmonella.

34. The method according to claim 25, wherein the inducible system is a phosphate depletion inducible system.

35. The method according to claim 25, wherein the polypeptide is assembled in the host cell.

36. The method according to claim 33, wherein the polypeptide is secreted into the periplasm of the host cell.

37. The method according to claim 25 wherein the polypeptide is an antibody.

38. The method according to claim 25, wherein the polypeptide is selected from the group consisting of an Fab'$_2$ antibody and an Fab antibody or other form of antibody.

39. The method according to claim 25, wherein the metabolic and growth rate of the host cells is maximized in step (a).

* * * * *